(12) United States Patent
Götte

(10) Patent No.: US 10,792,105 B2
(45) Date of Patent: *Oct. 6, 2020

(54) METHOD AND APPARATUS FOR DETERMINING IMPLANT POSITIONS OF TWO MEDICAL IMPLANT COMPONENTS FORMING A JOINT

(71) Applicants: Smith & Nephew, Inc., Memphis, TN (US); Smith & Nephew Asia Pacific Pte. Limited, Singapore (SG); Smith & Nephew Orthopaedics AG, Zug (CH)

(72) Inventor: Hubert Götte, Feldkirchen (DE)

(73) Assignees: Smith & Nephew, Inc., Memphis, TN (US); Smith & Nephew Asia Pacific Pte. Limited, Singapore (SG); Smith & Nephew Orthopedics AG, Zug (CH)

(*) Notice: Subject to any disclaimer, the term of this patent is extended or adjusted under 35 U.S.C. 154(b) by 0 days.

This patent is subject to a terminal disclaimer.

(21) Appl. No.: 16/406,551

(22) Filed: May 8, 2019

(65) Prior Publication Data

US 2019/0262079 A1 Aug. 29, 2019

Related U.S. Application Data

(63) Continuation of application No. 15/034,047, filed as application No. PCT/EP2013/076945 on Dec. 17, 2013, now Pat. No. 10,327,848.

(51) Int. Cl.
*A61B 34/10* (2016.01)
*A61F 2/46* (2006.01)
(Continued)

(52) U.S. Cl.
CPC .............. *A61B 34/10* (2016.02); *A61F 2/38* (2013.01); *A61F 2/4657* (2013.01);
(Continued)

(58) Field of Classification Search
CPC ........... A61F 2/38; A61F 2/4657; A61B 34/10
See application file for complete search history.

(56) References Cited

U.S. PATENT DOCUMENTS

| 5,880,976 A | 3/1999 | DiGioia, III et al. |
| 7,842,092 B2 * | 11/2010 | Otto .................... A61F 2/38 |
| | | 623/18.11 |

(Continued)

FOREIGN PATENT DOCUMENTS

| WO | 0236031 A1 | 5/2002 |
| WO | 2012123029 A1 | 9/2012 |

(Continued)

OTHER PUBLICATIONS

International Search Report, PCT/EP2013/076945, pp. 1-4, dated Jul. 25, 2014, NL.

*Primary Examiner* — Christine A Enad
(74) *Attorney, Agent, or Firm* — Troutman Pepper Hamilton Sanders LLP

(57) ABSTRACT

A data processing method, performed by a computer, for determining implant positions of two implant components relative to two bones, wherein each of the implant components is to be attached to one of the bones such that the implant components form a joint between the bones, and wherein an implant position is a relative position between the implant component and the corresponding bone, said method comprising the steps of:
  a) acquiring a set of target poses, wherein a target pose represents a relative position to be achieved between the two bones;
  b) calculating a set of virtual poses for a pair of virtual test implant positions, wherein the set of virtual poses comprises one virtual pose for each of the target poses and wherein a virtual pose represents a relative position (Continued)

Figure 1:
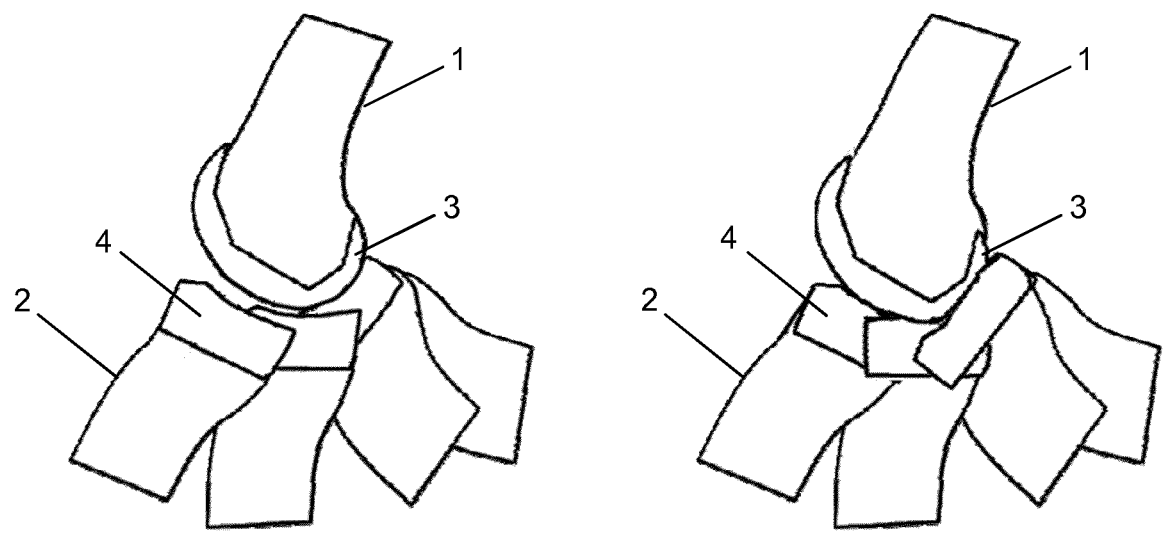

between the two bones if the virtual test implant positions were applied as the implant positions;

c) calculating a pose deviation value for each of the target poses, wherein a pose deviation value represents the difference between a target pose and the corresponding virtual pose;

d) calculating an overall pose deviation value from all the individual pose deviation values;

e) repeating steps b) to d) for different pairs of virtual test implant positions until the overall pose deviation value fulfils a minimisation criterion; and f) using the pair of virtual test implant positions for which the minimisation criterion is fulfilled as the implant positions.

17 Claims, 7 Drawing Sheets

(51) Int. Cl.
*A61F 2/38* (2006.01)
*A61F 2/30* (2006.01)

(52) U.S. Cl.
CPC ... *A61B 2034/104* (2016.02); *A61B 2034/107* (2016.02); *A61B 2034/108* (2016.02); *A61F 2002/30616* (2013.01); *A61F 2002/4633* (2013.01)

(56) References Cited

U.S. PATENT DOCUMENTS

| | | | | |
|---|---|---|---|---|
| 9,775,725 | B2* | 10/2017 | van der Walt | A61B 17/56 |
| 9,795,399 | B2* | 10/2017 | Metzger | A61B 17/1764 |
| 9,827,112 | B2* | 11/2017 | Bettenga | A61F 2/46 |
| 2004/0152970 | A1* | 8/2004 | Hunter | A61B 17/025 |
| | | | | 600/424 |
| 2004/0167390 | A1* | 8/2004 | Alexander | A61B 5/055 |
| | | | | 600/410 |
| 2007/0061014 | A1* | 3/2007 | Naegerl | A61F 2/389 |
| | | | | 623/20.31 |
| 2008/0269596 | A1* | 10/2008 | Revie | G06Q 10/087 |
| | | | | 600/424 |
| 2009/0043556 | A1* | 2/2009 | Axelson | G06F 17/50 |
| | | | | 703/11 |
| 2010/0076563 | A1* | 3/2010 | Otto | A61B 5/103 |
| | | | | 623/20.14 |
| 2014/0244220 | A1* | 8/2014 | McKinnon | A61F 2/02 |
| | | | | 703/1 |
| 2016/0217268 | A1* | 7/2016 | Otto | A61B 5/103 |

FOREIGN PATENT DOCUMENTS

| | | |
|---|---|---|
| WO | 2013083201 A1 | 6/2013 |
| WO | 2013083202 A1 | 6/2013 |
| WO | 2013083297 A1 | 6/2013 |
| WO | 2013101753 A1 | 7/2013 |

* cited by examiner

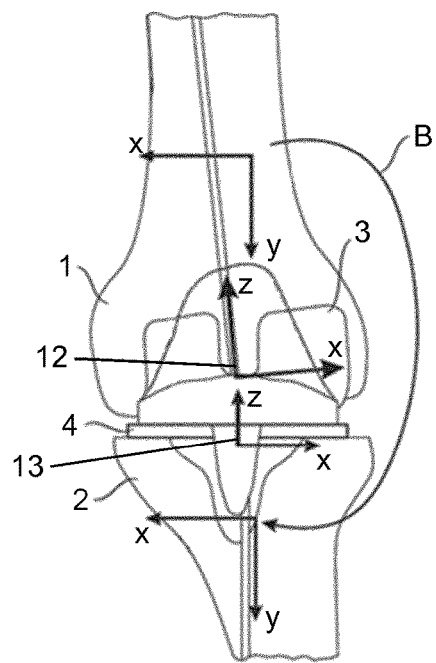 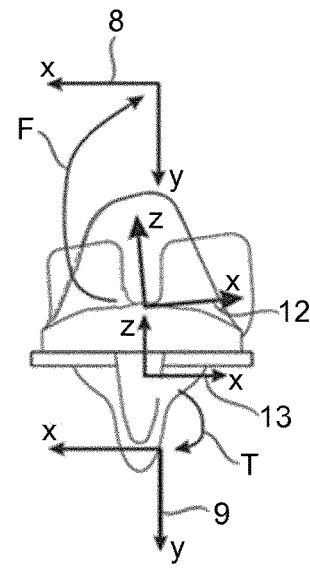 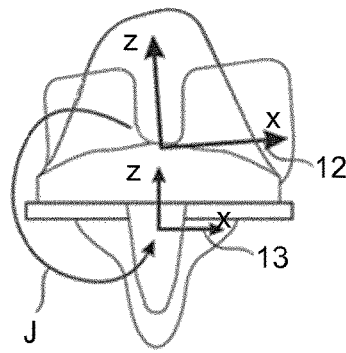
Figure 4a      Figure 4b      Figure 4c
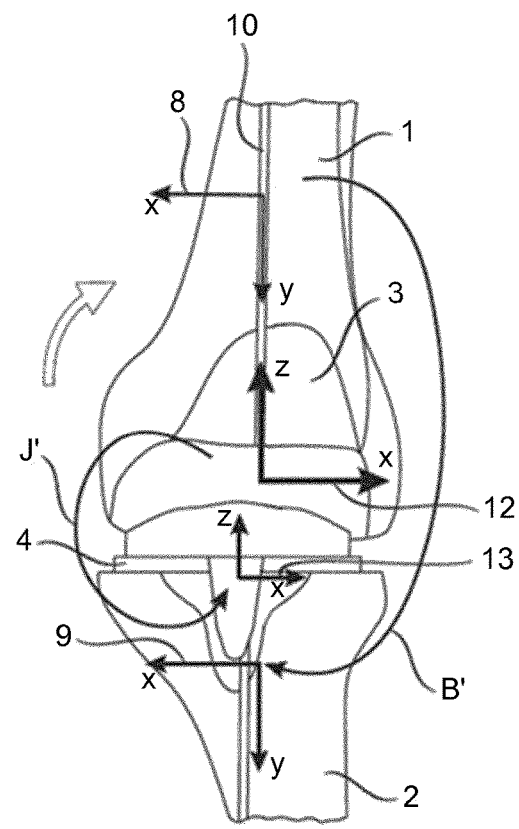
Figure 5

| Parameter | Leg Alignment | 6 DoF | Difference |
|---|---|---|---|
| $ml_t$ | -1.0 mm | -1.0 mm | |
| $ap_t$ | 0 mm | 0 mm | |
| $pd_t$ | 6.0 mm | 2.2 mm | -3.8 mm |
| $fe_t$ | 3.0° | 3.0° | 0° |
| $vv_t$ | 0° | 0° | |
| $ie_t$ | 0° | -0.5° | -0.5° |
| $ml_f$ | 0 mm | 0 mm | |
| $ap_f$ | 3.0 mm | 0 mm | -3.0 mm |
| $pd_f$ | 0 mm | -2.6 mm | -2.6 mm |
| $fe_f$ | 0° | 0° | |
| $vv_f$ | 0° | 0° | |
| $ie_F$ | -6.5° | -4.5° | 2.0° |

Figure 11

METHOD AND APPARATUS FOR DETERMINING IMPLANT POSITIONS OF TWO MEDICAL IMPLANT COMPONENTS FORMING A JOINT

RELATED APPLICATION DATA

This application is a Continuation application of U.S. application Ser. No. 15/034,047 filed on May 4, 2016, which is a national phase application of International Application No. PCT/EP2013/076945 filed on Dec. 17, 2013 and published in the English language. The entireties of such applications are incorporated herein by reference.

The present invention relates to a method and a device for determining implant positions of two implant components relative to two bones.

Replacing worn joints between two bones with artificial joints has become a standard medical procedure. In a typical approach, the parts of the two bones forming the original joint are removed and replaced with two implant components which interact with each other. An important factor in the success of the replacement, i.e. a correct kinematic functioning of the joint after the replacement, is that of finding a suitable position of the implant components relative to the bones which they are attached to. While this document focuses on knee joints, the present invention is equally applicable to other joints such as the elbow joint.

The relative position between an implant component and a bone is represented by six parameters corresponding to six degrees of freedom. These six degrees of freedom consist of three translational degrees of freedom and three rotational degrees of freedom. The directions of the translational degrees of freedom are preferably the proximodistal (pd) direction, the anterioposterior (ap) direction and the mediolateral (ml) direction, and the three rotational degrees of freedom are preferably represented by the flexion/extension (fe) angle, the internal/external (ie) angle and the varus/valgus (vv) angle. The positions of the two implant components are thus defined by twelve parameters for twelve degrees of freedom hence finding suitable implant positions means finding suitable values for these twelve parameters.

In a classic planning approach for computer assisted navigated total knee replacement, the implant components are rotationally aligned to basic bone directions and shifted into place. Each implant component position is established independently of the other, i.e. only considering the bone geometry and bone shape. Classic planning can result in poor kinematics of the joint after the replacement. Poor kinematics can cause problems for the patient, i.e. flexion and extension deficits of the postoperative joint, looseness or excessive stress for the ligaments as well as excessive wear of the implant components.

A more sophisticated approach is commonly referred to as the leg alignment approach. It aims to adapt the implant positions to the freedom and limits provided by the soft tissue, for example the cruciate and collateral ligaments. Two poses are used to individually optimise three dedicated position parameters. Typically, full extension and 90° of flexion are used as the two poses. For the tibial implant, the shift in the proximodistal direction ("pd shift") is adjusted. For the femoral implant, the shift in the anterioposterior direction ("ap shift") and the internal-external rotation ("ie rotation") are adjusted. A "pose" is a relative position between the two bones. The leg alignment approach is however limited in several aspects, one being that it only optimises three of the degrees of freedom of the implant positions.

In a first step with the knee joint at full extension, the femur and the tibia are actively aligned with their mechanical axes so as to fall in line. The surgeon manually applies a corrective force to the bones. As a result, the ligaments are stretched and the joint gap, i.e. the gap between the two bones within the joint, opens up on the side with the dominant bone loss. The planned tibial component position is shifted in the proximodistal direction until it touches the femoral implant in the aligned bone pose.

In a second step at a 90° flexion of the knee joint, the ap shift and the ie rotation of the planned femoral implant position are adjusted for parallel alignment and contact between the femoral implant and the tibial implant. The shift and rotations are calculated on the basis of implant thickness values provided by the implant manufacturer and the measurement of both the established poses in all or dedicated degrees of freedom.

In this document, the inventor proposes an improved planning approach as described in the independent claims. Advantageous embodiments are defined in the dependent claims.

The present invention relates to a data processing method, performed by a computer, for determining implant positions of two implant components relative to two bones, wherein each of the implant components is to be attached to one of the bones such that the implant components form a joint between the bones, and wherein an implant position is a relative position between the implant component and the corresponding bone. In this document, the term "position" means a spatial location in up to three translational dimensions and/or a rotational alignment in up to three rotational dimensions.

A first step of the method involves acquiring a set of target poses, wherein a target pose represents a relative position to be achieved between the two bones. The target poses can be provided using a number of approaches. In a first approach, sample poses of the two bones are recorded before joint replacement. In another approach, sampled poses of a corresponding joint are mirrored, wherein sampled poses of the right leg can for example be mirrored in order to be used as target poses for the left leg, and vice versa. In yet another approach, the target poses are hypothetical or predefined poses which represent the desired or ideal kinematics of the joint.

A second step of the method involves calculating a set of virtual poses for a pair of virtual test implant positions, wherein the set of virtual poses comprises one virtual pose for each of the target poses and wherein a virtual pose represents a relative position between the two bones that provides the intended mechanical interaction of the implant component surfaces, i.e. by having stable contact, and wherein the implant components are placed at the set of virtual test implant positions. In other words, the virtual test implant positions are assumed for the implant components. The virtual poses represent the relative positions between the two bones if the implant components were implanted using the assumed virtual test implant positions and interact in their mechanically intended way. The mechanically intended way of interaction in particular requires stable implant component contact without overlap or gap.

A virtual pose shall approximate the real pose that the joint would escape to with the implant components implanted and the target pose applied. The real pose depends, besides the implant positions, on the target pose, on the shape of the implant components and on the mechanical interaction of all the bony and the soft tissue structures, such as ligaments, tendons and muscles, of the joint. The virtual pose can be determined considering all possible factors as mentioned above or by using a simplified approach with a reduced set of factors as explained below in more detail.

Calculating a virtual pose in particular can comprise some sort of modelling the behaviour of the bony and soft tissue structures. In particular, the potential position changes from the target pose to the virtual pose can be restricted to dedicated degrees of freedom to establish preferred elongation directions of ligaments or muscle fibres. While, in general, many virtual poses might exist for a pair of virtual test implant positions and a target pose, this restriction preferably results in just one virtual pose.

A third step of the method involves calculating a pose deviation value for each of the target poses, wherein a pose deviation value represents the difference between a target pose and the corresponding virtual pose. This means that the pose deviation value indicates the degree of similarity between a target pose and the corresponding virtual pose for a particular pair of virtual test implant positions.

A fourth step involves calculating an overall pose deviation value from all the individual pose deviation values. The overall pose deviation value therefore represents the degree of similarity for all the target poses and all the virtual poses and is thus an indicator for the overall appropriateness of the assumed pair of virtual test implant positions.

In a fifth step, the second to fourth steps are repeated for different pairs of virtual test implant positions until the overall pose deviation value fulfils a minimisation criterion.

In other words, the best possible pair of virtual test implant positions is determined. The minimisation criterion can be a simple threshold value, such that iteration is discontinued once the overall pose deviation value for a particular pair of test implant positions falls below the threshold value. Alternatively, the minimisation criterion can be a minimum, such as a local minimum or preferably a global minimum. This means that the steps are repeated until, for a particular set of pairs of virtual test implant positions, the pair of test implant positions for which the overall pose deviation value is a minimum is found.

A sixth step involves using the pair of virtual test implant positions for which the minimisation criterion is fulfilled as the implant positions, in particular as the final implant positions for a surgical therapy plan. This pair then represents the preferred implant position which will achieve the greatest congruency of target and virtual bone poses and which result in the best possible kinematic properties of the joint.

In accordance with the present invention, a plurality of target poses are used to determine the implant positions. The set of target poses preferably comprises at least three poses, even more preferably at least 5, 10, 15, 20 or more poses. Using this approach, the kinematics of the joint can be optimised over its whole range of motion (ROM) instead of for full extension and 90° flexion only, as with the leg alignment approach. In addition, the leg alignment approach only considers three degrees of freedom for the two components together, whereas the the invention can optimise any desired number of degrees of freedom for the implant positions which actually have twelve degrees of freedom (six degrees of freedom for one implant component and six degrees of freedom for the other implant component). Moreover, the parameters for the degrees of freedom considered are not determined one after the other but rather jointly, which respects potential interdependencies of the implant positions.

As described above, a virtual pose represents the relative position between the two bones, assuming the implant components are attached to the bones in the corresponding virtual test implant positions. A virtual pose is a pose which the two bones would actually assume, i.e. a functional pose involving a specific contact between the implant components. In the case of a knee joint, such contact is achieved when the condyles of the femoral implant are in stable contact with the corresponding plateaus of the tibial implant. In the method according to the present invention, calculating a virtual pose therefore preferably involves determining a relative position between the implant components in which they are in stable contact. As indicated above, stable contact applies when the two implant components are in contact at at least two contact points. It will be obvious that said relative position between the implant components must correspond to a natural pose of the bones, i.e. a pose which is within the regular functional range of the joint.

As outlined above, a virtual pose is a relative position and is therefore defined by up to six parameters corresponding to six degrees of freedom, namely up to three translational degrees of freedom and up to three rotational degrees of freedom.

As explained above, the position of an implant component relative to the bone has six degrees of freedom. The relative position of the implant component has to be defined with respect to a reference of the bone, such as a co-ordinate system of the bone, which is also referred to as a bone co-ordinate system. The bone co-ordinate system is preferably a Cartesian co-ordinate system. The location of the origin of a bone co-ordinate system and the orientation of its axes can generally be selected arbitrarily. However, it is preferable to align the axes of the bone co-ordinate system so as to be parallel with anatomical bone axes such as for example the mechanical axis. Preferably, one axis of the co-ordinate system extends in a proximodistal direction ("pd direction"), which for example equates with the mechanical axis of a femur or a tibia, while another axis extends in the mediolateral direction ("ml direction") and yet another axis extends in the anteroposterior direction ("ap direction"). A rotation about the proximodistal axis ("pd axis") is an internal/external rotation ("ie rotation"), a rotation about the mediolateral axis ("ml axis") is a flexion/extension rotation ("fe rotation"), and a rotation about the anteroposterior axis ("ap axis") is a varus/valgus rotation ("vv rotation"). The absolute location of the origin of the bone co-ordinate system is irrelevant, although the origin has to be kept constant with respect to the bone.

Using a bone co-ordinate system as described above, the position of an implant component can be described by six parameters which can be combined into a vector. In the case of a knee joint, the position of the tibial implant can be described by $pos_{tibia} = (ml_t, ap_t, pd_t, vv_t, ie_t, fe_t)^T$ and the position of the femoral implant can be described by $pos_{femur} = (ml_f, ap_f, pd_f, vv_f, ie_f, fe_f)^T$. A pose, i.e. a relative position between the two bones, can also be described by six parameters for the six degrees of freedom. A pose is preferably represented by the relative position of a co-ordinate system of one of the bones in the co-ordinate system of the other bone. These two co-ordinate systems of the bones are preferably the same bone co-ordinate systems as those used to describe the implant component positions, though they need not be.

Preferably, each implant component also has a co-ordinate system assigned to it as a reference; these co-ordinate systems are also referred to as implant co-ordinate systems. The implant position of one implant component relative to the corresponding bone can then be expressed as the relative position between the bone co-ordinate system and the implant co-ordinate system. The implant co-ordinate systems are preferably Cartesian co-ordinate systems, the axes of which preferably match the ml, ap and pd directions, in particular those locally assigned to the implant component. The relative position between a bone co-ordinate system and an implant co-ordinate system can be described by a transformation, such as a vector comprising the six parameters as described above or a 4×4 transformation matrix. For example, a matrix F describes the transformation of the femoral bone co-ordinate system into the femoral implant co-ordinate system, and a matrix T describes a transformation of the tibial bone co-ordinate system into the tibial implant co-ordinate system.

In one embodiment, a pose is represented by the relative position of the implant co-ordinate systems. The transformation matrices F and T are known and constant for a given pair of implant positions. A pose represented by a transformation matrix B which represents the transformation of one bone co-ordinate system into the other bone co-ordinate system can then be used to calculate a transformation matrix J which describes the pose between the two implant co-ordinate systems. For the same pose B, the transformation matrix J depends on the implant positions, i.e. the matrices F and T and can be calculated as $J=F*B*T^{-1}$. A set of target poses represented by a set of transformation matrices B can therefore also be expressed as a set of target poses represented by transformation matrices J for fixed transformation matrices F and T.

In other words, a pose represented by the relative position of the (bone) co-ordinate systems which are not co-ordinate systems of the implant components is transformed into a pose represented by the relative position of the co-ordinate systems of the implant components. In this document, a pose can be a bone pose or a joint pose, depending on the references used. A target pose can thus be a target bone pose or a target joint pose and a virtual pose can be a virtual bone pose or a virtual joint pose.

The transformation J describes the relative position between the two implant components and can therefore be referred to as the implant pose. The implant pose J is not necessarily a pose in which the two implant components are in stable contact.

For each of the target joint poses J, a corresponding virtual implant joint pose J' therefore has to be found in which the implant components are in particular in stable contact. A virtual implant pose J' can be converted, via the transformations F and T, into a bone pose B' which is a virtual bone pose. Since the implant co-ordinate systems are assigned to the implants and are therefore very close to the joint, the difference between a target joint pose J and the corresponding virtual joint pose J' can easily be interpreted by a physician because it represents meaningful values of the joint kinematics expressed as shifts along and rotations around main physiological directions. Transforming a bone pose into a joint pose or vice cersa is explained in detail in patent application PCT/EP2011/072324, which is hereby incorporated by reference.

There are a number of different possible ways of finding a virtual pose that provides the intended mechanical interaction of the implant component surfaces, i.e. by having stable contact. One basic approach is to simply test a plurality of poses until a suitable pose is found. However, a multitude of more sophisticated approaches also exist.

In one embodiment, all but two parameters are fixed and the remaining two parameters are varied until a stable contact is achieved. If, in particular, a virtual pose, and preferably a virtual joint pose, is defined by six parameters corresponding to six degrees of freedom, then calculating a virtual pose involves fixing four of the six parameters and varying the remaining two parameters until a stable contact is achieved. In a particular embodiment, the parameters for the ml shift, the ap shift, the ie rotation and the fe rotation are fixed and the parameters for the pd shift and the vv rotation are determined. This approach is advantageous in that it obtains a virtual pose, in particular a virtual bone pose, which very likely matches the pose the bones would actually take if the implants were attached to the bones with the corresponding pair of test implant positions, in particular since the ligaments create a force between the bones which mainly causes a pd movement and a moment which results in a w rotation.

More details regarding this approach are described in the patent application PCT/EP2012/061757, which is hereby incorporated by reference. In this document, one approach involves selecting an initial relative position and bringing the two bones together translationally until they are in contact at a first contact point. The approach is then continued until there is a contact at a second contact point. The distance in the direction of approach between the first and second contact points is used to determine a rotation such that the two bones are in stable contact. In an alternative approach, the first contact point is determined, and one of the bones is then rotated about the first contact point until there is stable contact between the two bones. In both approaches, values for the parameters in one rotational degree of freedom and one translational degree of freedom are determined for constant values of the other parameters. This approach is preferably applied if a virtual joint pose is determined, because a virtual joint pose is based on physiologically meaningful directions close to the joint as explained above.

Another approach for calculating a virtual pose is disclosed in the patent application PCT/EP2011/072323, which is also hereby incorporated by reference. In this approach, a plurality of poses in which two bones are in stable contact are given. A virtual pose, for example for a particular flexion angle, is then determined from the known poses, for example by interpolation or extrapolation. This approach, too, is preferably applied if a virtual joint pose is determined, because determining the virtual joint pose is mostly independent of the virtual test implant positions. This is because stable contact depends on the shape of the implants rather than their positions relative to the bones. This means that only one set of poses in which the two bones are in stable contact is required which can be interpolated or extrapolated.

As explained above, one step of the method involves calculating a pose deviation value for each of the target poses. A pose deviation value is a single numerical value assigned to the particular difference between a target pose B and a virtual pose B' or equally between a target implant pose J and a virtual implant pose J'. The computational rule for calculating a pose deviation value from the difference between a target pose and a virtual pose, which also comprises up to six parameters for the six degrees of freedom, is not particularly limited and can be selected as appropriate. Calculating the pose deviation value can for example involve weighting the parameters.

In one embodiment, which is particularly relevant in combination with calculating a virtual pose using four fixed parameters and determining one translational and one rotational parameter as described above, the pose deviation value is calculated from the deviation between a virtual pose and a corresponding target pose, and preferably between a virtual joint pose and a corresponding target joint pose, with respect to a varus-valgus rotation ("vv rotation") and a proximodistal shift ("pd shift") only. Since the other four parameters are constant, they can be disregarded when calculating the pose deviation value. A pose deviation value can then in particular be calculated using the equation $$\text{poseDeviationValue} = [(pd_{J'} - pd_{J'})^2 + (vv_{J'} - vv_{J'})^2]^{1/2}.$$

In another embodiment, a pose deviation value is calculated from the distances between each of two points on one of the bones and corresponding points on the other bone. In the case of a knee joint, these four points on the two bones are the points at which the collateral ligaments are connected to the bones. The points at which the ligaments are connected to the femur can be approximated as being the epicondylar points of the femur. A pose deviation value can then be calculated in an alternative fashion from the distances between each of the two epicondylar points and a transverse plane which extends through the tibia, in particular using the equation $$\text{poseDeviationValue} = [(epiM_J - epiM_{J'})^2 + (epiL_J - epiL_{J'})^2]^{1/2},$$

where epiM is the distance between the medial epicondyle of the femur and the transverse plane, epiL is the distance between the lateral epicondyle of the femur and the transverse plane, and J and J' are indices for the target pose and the virtual pose, respectively. Even though J and J' are used as indices, the target pose and the virtual pose need not be a target joint pose and a virtual joint pose, but could likewise be a target bone pose and a virtual bone pose.

Calculating the overall pose deviation value from all the individual pose deviation values can involve calculating the sum of the pose deviation values or the square root of the sum of the squares of the pose deviation values. In one embodiment, the overall pose deviation value is calculated from weighted pose deviation values. In this embodiment, the influence of particular poses can be reduced or emphasised. Preferably, at least one of the weightings is not 1.

The virtual test implant positions can generally be chosen arbitrarily, i.e. any virtual test implant position which satisfies the minimisation criterion can be selected, even though it may represent a surgically or physiologically undesirable position at the bone. In one embodiment of the present invention, boundaries are therefore defined for the virtual test implant positions. The boundaries are in particular defined by value ranges for the parameters for the six degrees of freedom of each virtual test implant position.

As described above, a virtual test implant position is defined by six parameters corresponding to six degrees of freedom, thus resulting in twelve degrees of freedom for the two implant components. In one embodiment, the virtual test implant positions are varied in less than twelve degrees of freedom, and the parameters for the remaining degrees of freedom are set to fixed values. The parameters for the remaining degrees of freedom can then for example be determined using the classic planning approach or the leg alignment approach. The following list comprises example scenarios for the degrees of freedom in which the virtual test implant positions can be varied. In these scenarios, the varied parameters are:

1. $pd_t$, $ap_f$ and $ie_f$;
2. $pd_t$, $ap_f$, $ie_f$ and $pd_f$;
3. $pd_t$, $ap_f$, $ie_f$, $pd_f$ and $ie_t$;
4. $pd_t$, $ap_f$, $ie_f$, $pd_f$, $ie_t$ and $fe_t$; and
5. $pd_t$, $ap_f$, $ie_f$, $pd_f$, $ie_t$, $fe_t$ and $vv_t$.

The target poses can be determined from image data of the bones which are captured for different poses of the bones using marker devices which are attached to the bones and tracked using a medical navigation system or any other suitable approach.

The present invention also relates to a program which, when running on a computer, causes the computer to perform the steps of the method as described above and/or to a program storage medium on which the program is stored and/or to a computer comprising such a program storage medium and/or to a signal wave, in particular a digital signal wave, carrying information which represents the program.

The present invention also relates to a device for determining implant positions of two implant components relative to two bones, comprising a computer onto which the program as described above is loaded.

The method in accordance with the invention is in particular a data processing method. The data processing method is preferably performed using technical means, in particular a computer. The data processing method is preferably constituted to be executed by or on a computer and in particular is executed by or on the computer. In particular, all the steps or merely some of the steps (i.e. less than the total number of steps) of the method in accordance with the invention can be executed by a computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. In particular, the term "cloud" is used in this respect as a metaphor for the Internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or which are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer.

The expression "acquiring data" in particular encompasses (within the framework of a data processing method) the scenario in which the data are determined by the data processing method or program. Determining data in particular encompasses measuring physical quantities and transforming the measured values into data, in particular digital data, and/or computing the data by means of a computer and in particular within the framework of the method in accordance with the invention. The meaning of "acquiring data" also in particular encompasses the scenario in which the data are received or retrieved by the data processing method or program, for example from another program, a previous method step or a data storage medium, in particular for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are in particular detected or captured (for example by an analytical device). Alternatively or additionally, the data are inputted in accordance with the additional step, for instance via interfaces. The data generated can in particular be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, in particular determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

In particular, the invention does not involve or in particular comprise or encompass an invasive step which would represent a substantial physical interference with the body requiring professional medical expertise to be carried out and entailing a substantial health risk even when carried out with the required professional care and expertise. In particular, the invention does not comprise a step of positioning a medical implant in order to fasten it to an anatomical structure or a step of fastening the medical implant to the anatomical structure or a step of preparing the anatomical structure for being fastened to the medical implant. More particularly, the invention does not involve or in particular comprise or encompass any surgical or therapeutic activity. For this reason alone, no surgical or therapeutic activity and in particular no surgical or therapeutic step is necessitated or implied by carrying out the invention.

Figure 2:
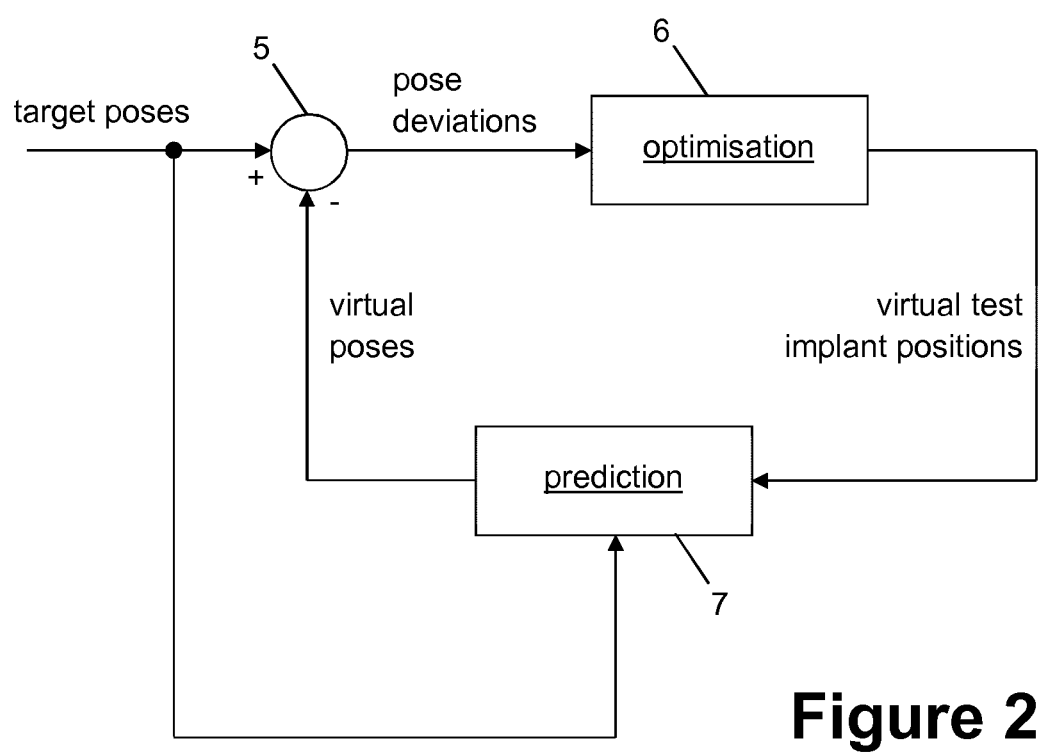
Figure 3A:
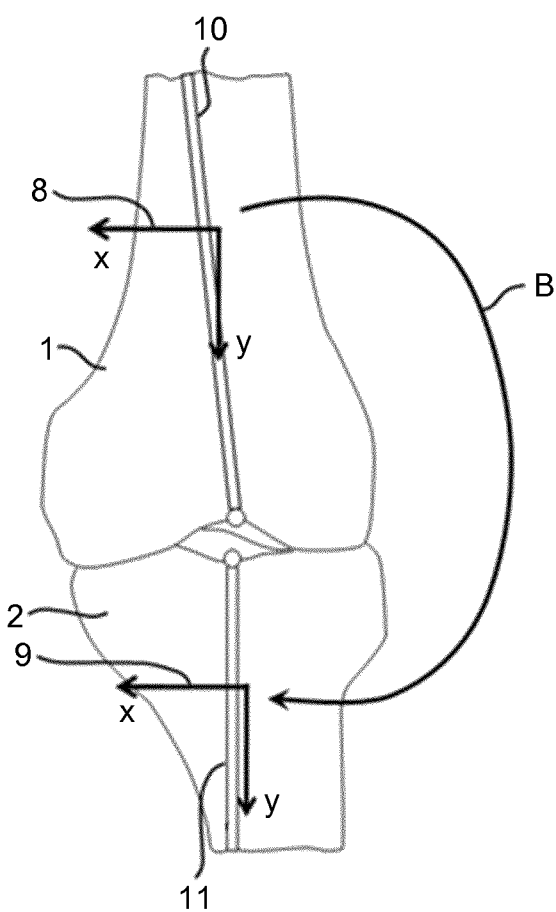
Figure 3B:
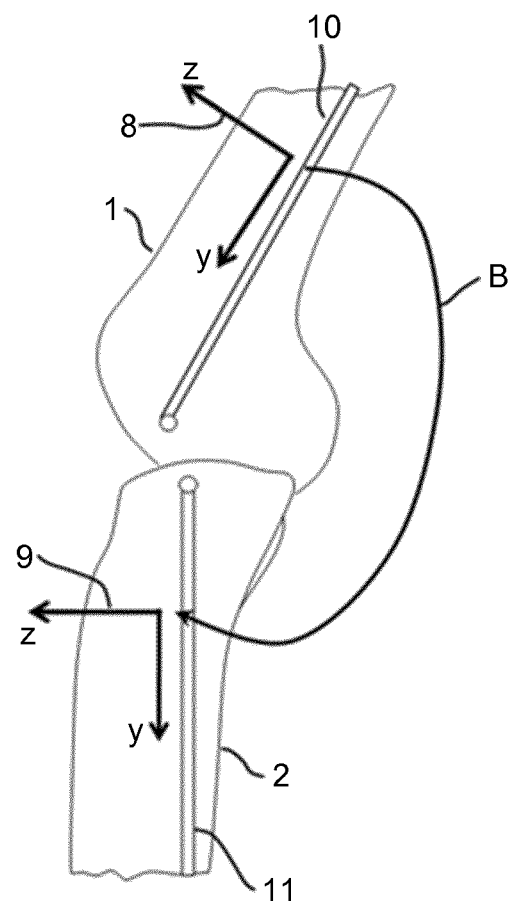
Figure 6:
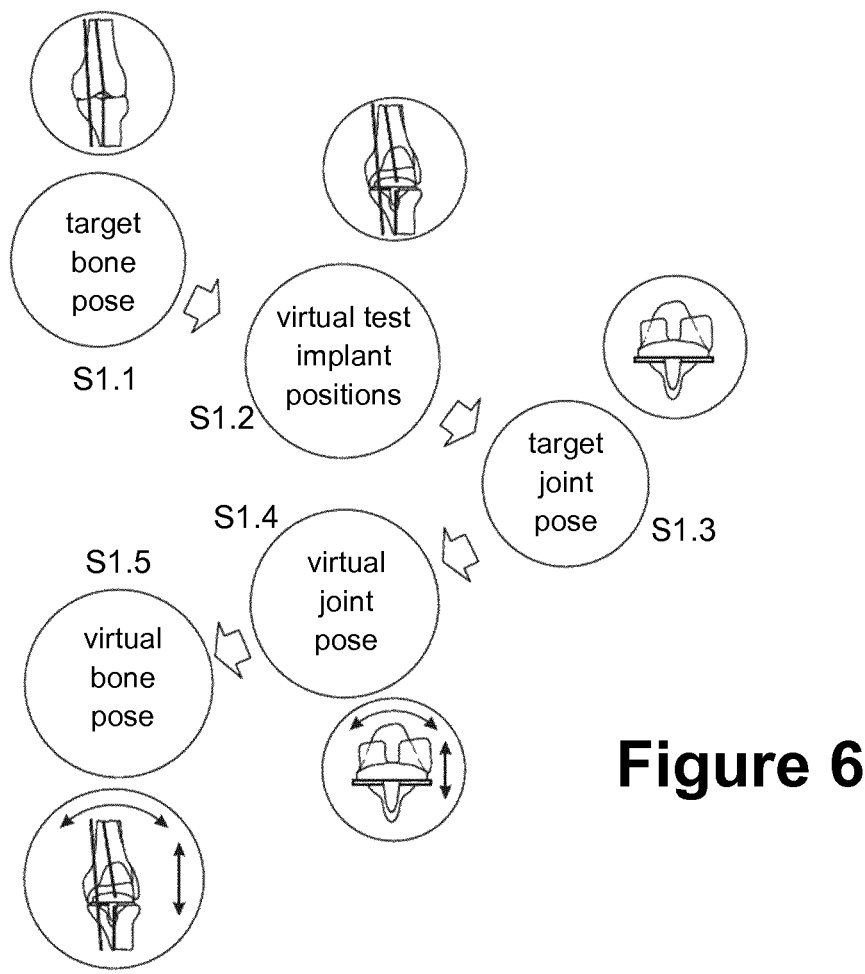
Figure 7:
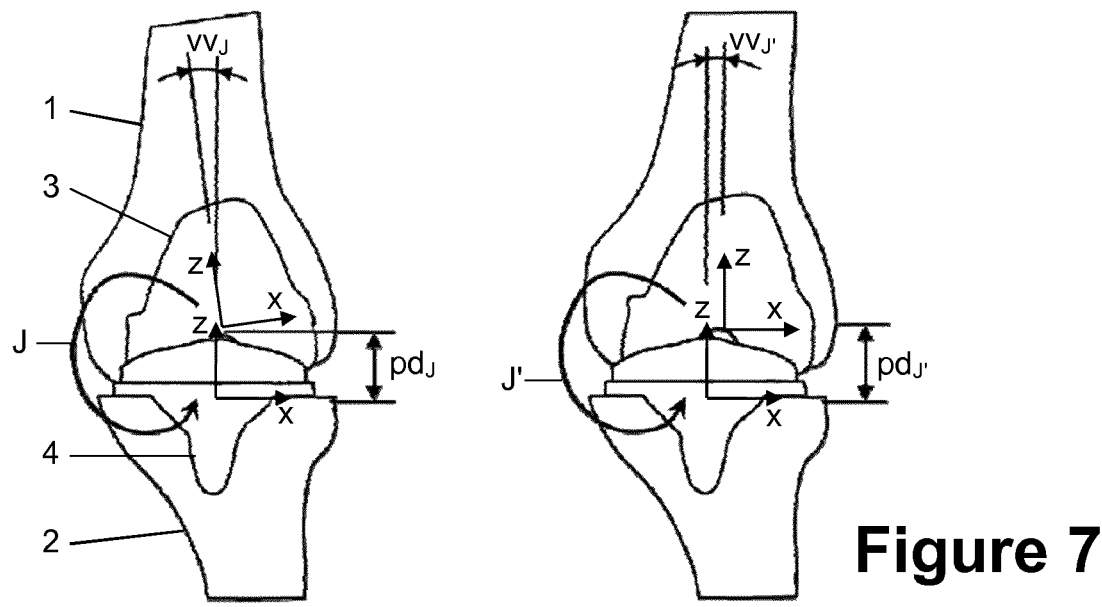
Figure 8:
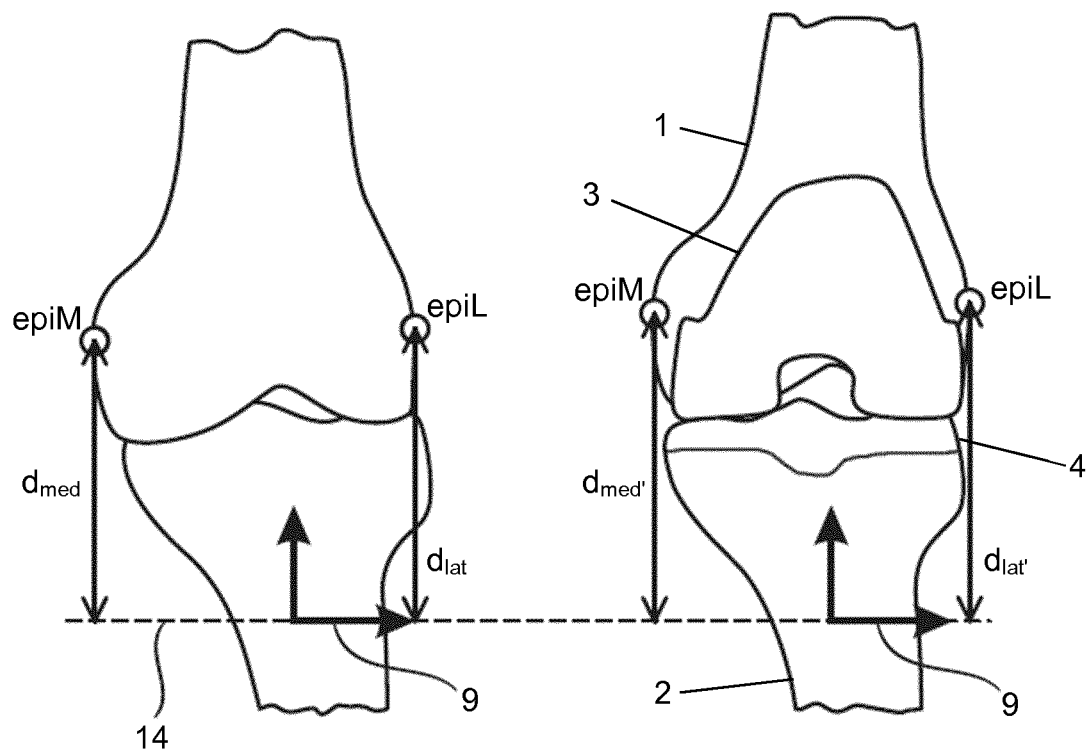
Figure 9:
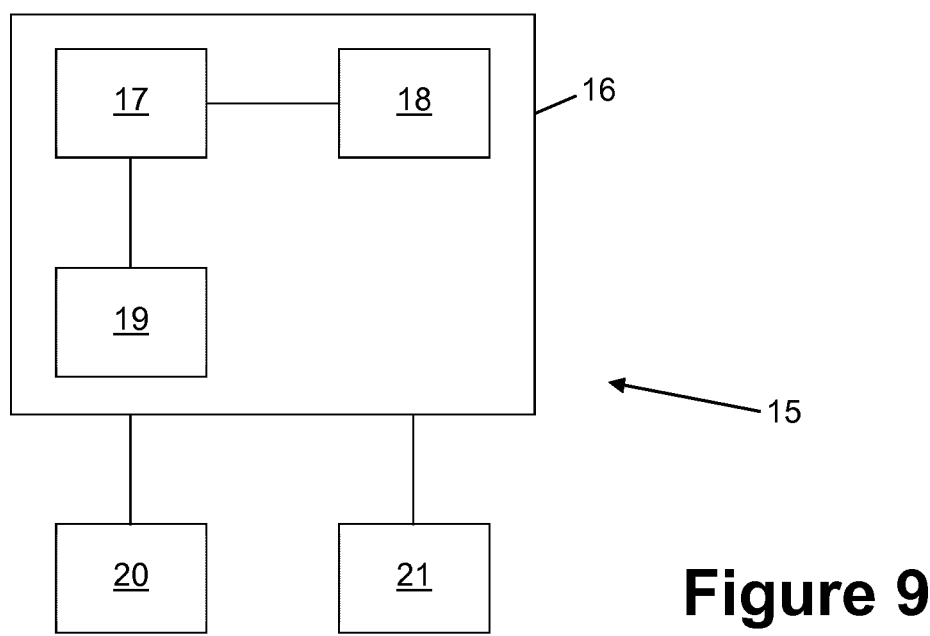
Figure 10A:
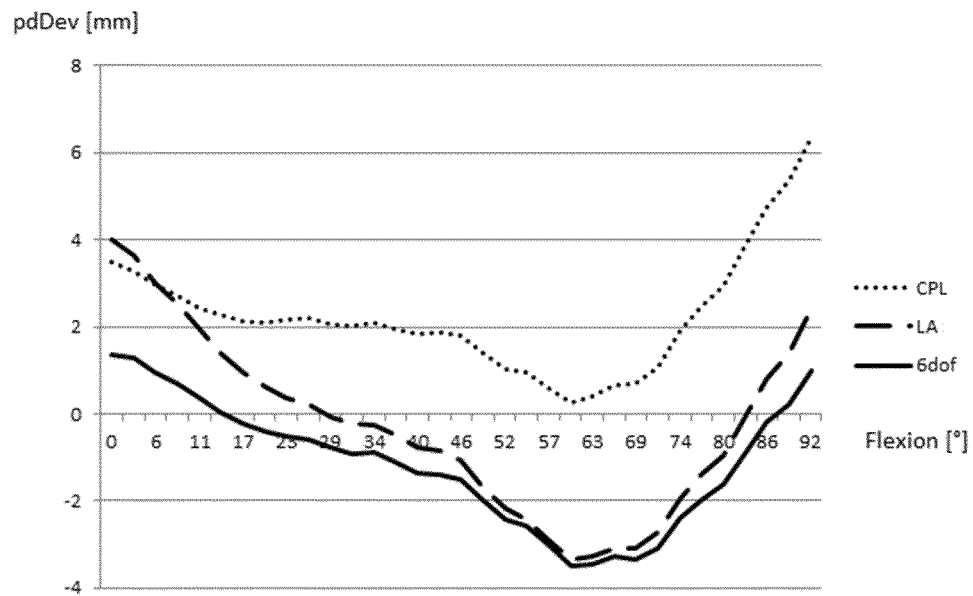
Figure 10B:
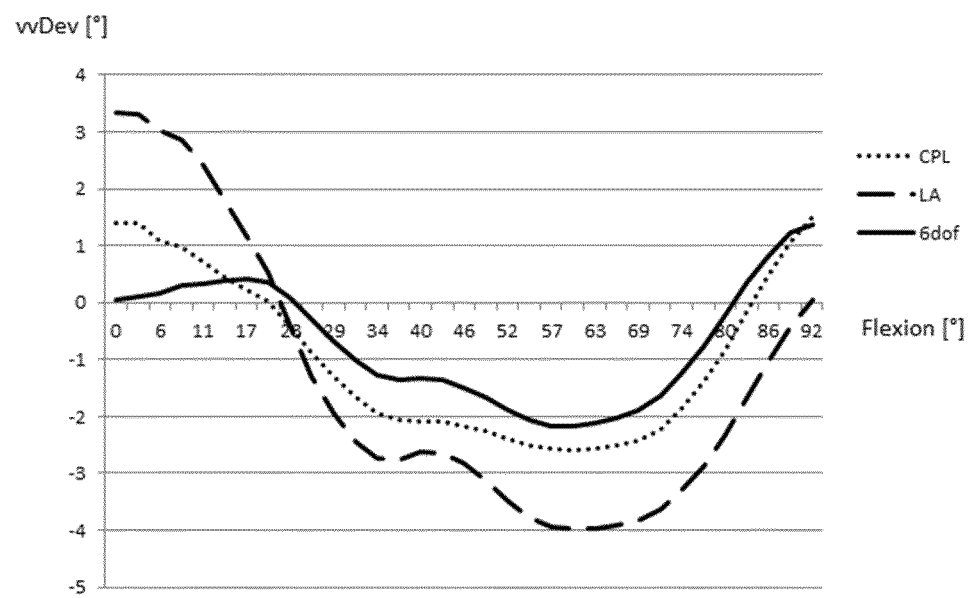

In the following, example embodiments of the invention are described with reference to the figures which illustrate the invention merely by way of example and do not limit the scope of the invention to the specific embodiments illustrated, and which show:

FIG. 1 a plurality of poses for different implant positions;

FIG. 2 a block diagram illustrating a process for determining the implant positions;

FIGS. 3a, 3b a single pose of the joint, viewed from two directions perpendicular to one another;

FIGS. 4a to 4c the transformation of a bone pose into an implant pose;

FIG. 5 a virtual pose;

FIG. 6 steps for determining a virtual bone pose for a target bone pose;

FIG. 7 a first example of calculating a pose deviation value;

FIG. 8 a second example of determining a pose deviation value;

FIG. 9 a computer for carrying out the method according to the invention;

FIGS. 10a, 10b graphs showing deviations between target poses and virtual poses determined using the classic planning, leg alignment and the present invention, respectively, over the range of motion; and FIG. 11 comparative results for the implant position results for the leg alignment approach and the approach in accordance with the present invention.

The left-hand illustration in FIG. 1 shows a plurality of bone poses, wherein a bone pose is a relative position between two bones. FIG. 1 illustrates the overall working principle of the invention. In the present example, the two bones are a femur 1 and a tibia 2 and the bone poses correspond to different flexion angles of the knee joint which connects the femur and the tibia. The femur 1 comprises a femoral implant component 3, and the tibia 2 comprises a tibial implant component 4. The implant components form an artificial knee joint. The implant positions shown in the left-hand illustration in FIG. 1 represent a classic approach. The bone poses represent example target bone poses, which are for example poses which the knee joint assumed prior to the introduction of an artificial knee joint.

As can be seen from FIG. 1, there are some poses in which there would be a gap between the femoral implant 3 and the tibial implant 4, and some poses in which the implants would overlap each other, once the implant components had been attached. In the latter case, the bones would move away from each other since such an overlap is not possible in reality. This would result in a loose knee joint in the poses exhibiting a gap, and a significant stress on the ligaments in the poses exhibiting overlapping implants. The gaps and overlaps between the implant components 3 and 4 in FIG. 1, and in particular in the left-hand illustration in FIG. 1, are exaggerated in order to accentuate the effect of the present invention.

The right-hand illustration in FIG. 1 represents the femur 1 and the tibia 2, together with the attached femoral implant component 3 and the attached tibial implant component 4, for the same poses as in the left-hand illustration, but with optimised implant positions. It can be seen that there are only small gaps or overlaps between the implant components, which means that the kinematics of the original knee joint are matched quite well.

FIG. 2 shows a block diagram which illustrates an approach for determining the implant positions. The diagram includes an adding block 5, an optimisation block 6 and a prediction block 7. A set of target poses is fed into the adding block 5 and the prediction block 7. The prediction block 7 calculates a set of virtual poses for a pair of virtual test implant positions. The set of virtual poses comprises one virtual pose for each of the target poses. A virtual pose is a hypothetical pose for a particular pair of implant positions. A virtual pose is a pose in which the implant components 3 and 4 are in stable contact, which means that they are in contact at at least two points. In other words, a virtual pose is a pose into which the joint, and thus the bones, are forced due to the mechanical interaction of the implant components when they are placed at the assumed pair of virtual test implant positions.

In a first iteration, the prediction block 7 uses an initial pair of virtual test implant positions which can comprise arbitrary virtual test implant positions or pre-calculated virtual test implant positions. A set of virtual poses is then provided to the adding block 5, where each virtual pose is subtracted from its corresponding target pose, thus resulting in a set of difference poses between the target poses and the virtual poses.

This set of difference poses is provided to the optimisation block 6 which calculates a pose deviation value for each of the target poses, wherein a pose deviation value represents a single numeric value corresponding to the difference between a target pose and the corresponding virtual pose.

The optimisation block 6 calculates an overall pose deviation value from the plurality of individual pose deviation values. If this overall pose deviation value fulfils a predetermined minimisation criterion, then the set of virtual test implant positions used by the prediction block 7 is outputted as the implant positions. If the overall pose deviation value does not fulfil the minimisation criterion, the optimisation block 6 determines a new pair of virtual test implant positions which is then provided to the prediction block 7 in order to calculate a new set of virtual poses.

The optimisation block 6 can select the new pair of virtual test implant positions by sequentially selecting pairs of virtual test implant positions from a list of pairs of virtual test implant positions. Alternatively, however, the optimisation block 6 can also implement an optimisation algorithm which determines the new pair of virtual test implant positions from at least one of the overall pose deviation values corresponding to the previously analysed pairs of virtual test implant positions.

FIGS. 3a and 3b show the femur 1 and the tibia 2 in a particular pose in a frontal and a lateral view, respectively. As can be seen from FIGS. 3a and 3b, a femoral co-ordinate system 8 is assigned to the femur 1, and a tibial co-ordinate system 9 is assigned to the tibia 2. The co-ordinate systems 8 and 9, which are also referred to as bone co-ordinate systems, have an invariable location and orientation relative to the respective bones which they are assigned to. In this example embodiment, the orientations of the bone co-ordinate systems 8 and 9 is such that their y-axis extends in a proximodistal direction, their x-axis extends in a mediolateral direction, and their z-axis extends in an anteroposterior direction when the leg is in its neutral position. FIGS. 3a and 3b also show the mechanical axis 10 of the femur 1 and the mechanical axis 11 of the tibia 2.

As can be seen from FIGS. 3a and 3b, the bone pose—i.e. the relative position between the femur 1 and the tibia 2—can be expressed as a transformation B which transforms the femoral co-ordinate system 8 into the tibial co-ordinate system 9 or vice versa. The transformation B can also be referred to as the bone pose B and is preferably one of the target poses from the set of target poses.

FIG. 4a shows the bones 1 and 2 from FIG. 3a, with the femoral implant component 3 and the tibial implant component 4 attached, for an assumed pair of virtual test implant positions. For the target bone pose B shown in FIG. 4a, the implant components 3 and 4 would overlap each other on the left side and provide a gap on the right side, thus resulting in an technically impossible and physiologically undesired pose if the implant components 3 and 4 were attached using the assumed pair of virtual test implant positions. The relative position between the femur 1 and the tibia 2 therefore has to be amended such that the femoral implant 3 and the tibial implant 4 are in stable contact at at least two contact points. This results in a virtual bone pose which corresponds to one particular target bone pose and depends on the assumed pair of virtual test implant positions.

As can be seen from FIGS. 4a and 4b, a femoral implant co-ordinate system 12 is assigned to the femoral implant 3, and a tibial implant co-ordinate system 13 is assigned to the tibial implant 4. The implant components 3 and 4 typically have a planar region which is to be placed onto a corresponding cutting plane of the bone to which it is to be attached. The z-axis of the implant co-ordinate systems is preferably perpendicular to this planar region, while the x-axis extends in the mediolateral direction of the implant component and the y-axis extends perpendicular to both the z-axis and the x-axis. The origin of the implant co-ordinate systems is preferably in the middle of the respective planar region.

The relative position between an implant component and the corresponding bone can be described by a transformation between the implant co-ordinate system and a corresponding bone co-ordinate system. FIG. 4b shows a transformation F between the femoral implant co-ordinate system 12 and the femoral bone co-ordinate system 8 and a transformation T between the tibial implant co-ordinate system 13 and the tibial bone co-ordinate system 9. Since the transformations F and T are constant for a particular pair of virtual test implant positions, the bone pose B can be converted into a joint pose J, shown in FIG. 4c, via the transformations F and T using the equation $$J = F * B * T^{-1},$$

where J, F, B and T are defined as 4×4 matrices.

The implant pose or transformation J describes the relative position between the two implant co-ordinate systems 12 and 13 for a particular transformation B between the bone co-ordinate systems 8 and 9 and a particular pair of virtual test implant positions. As already explained above, a transformation between two co-ordinate systems comprises six parameters, namely three translational shifts and three rotations. These six parameters are appropriately encoded into the 4×4 matrices J, B, F and T.

As explained above, attaching the implant components 3 and 4 to the bones 1 and 2, respectively, using the assumed pair of virtual test implant positions could result in an undesirable relative position between the bones 1 and 2, in which the implant components 3 and 4 overlap each other or are not in stable contact. The prediction block 7 (FIG. 2) therefore determines a virtual pose which corresponds to a target pose in which the implant components 3 and 4 are in stable contact with each other. This results in a virtual joint pose J' as shown in FIG. 5. Since the transformations F and T are constant, the virtual bone pose B' can be calculated from J', F and T.

In this embodiment, the approach described in patent application PCT/EP2012/061757 is applied in order to determine a virtual joint pose J' which is then transformed into the virtual bone pose B'. The parameters for the ap shift, the ml shift, the ie rotation and the fe rotation are kept constant and the parameters for the pd shift and the w rotation are determined such that the implant components 3 and 4 are in stable contact. Details will be described below with reference to FIG. 7.

The optimisation block 6 then calculates a pose deviation value for each target pose on the basis of the difference between the target pose and the corresponding virtual pose. It can be calculated on the basis of a target bone pose and a virtual bone pose or on the basis of a target joint pose and a virtual joint pose. The difference between a target joint pose J and a virtual joint pose J' is however easier for a physician to analyse if it is presented as deviations in the ml, ap and pd shifts and the ie, fe and w rotations.

FIG. 6 summarises how a virtual bone pose is calculated for a target bone pose. In step S1.1, a target bone pose is selected. In step S1.2, a pair of virtual test implant positions is selected. In step S1.3, a target joint pose is calculated from the target bone pose and the pair of virtual test implant positions. In step S1.4, a virtual joint pose in which the implant components are in stable contact is calculated. In step S1.5, a virtual bone pose corresponding to the target bone pose is calculated from the virtual joint pose and the pair of virtual test implant positions.

FIG. 7 shows a femur 1 with a femoral implant 3 and a tibia 2 with a tibial implant 4 in a target pose and a virtual pose, in order to explain an approach for calculating a virtual pose which corresponds to a target pose. The left-hand illustration in FIG. 7 shows the bones with the implant components for a particular pair of virtual test implant positions in the target pose which exhibits the parameter values $vv_J$ and $pd_J$. The virtual test implant positions cause the implants 3 and 4 to overlap each other. In this example approach, the parameters ml, ap, ie and fe are kept constant, and the pd parameter of the target joint pose J is changed such that there is a gap between the femoral implant 3 and the tibial implant 4.

The bones 1 and 2 are then brought together in the pd direction until the femoral implant 3 and the tibial implant 4 are in contact with each other. If there is no stable contact, i.e. only contact at a single point, then the approach is continued until there is contact between the femoral implant 3 and the tibial implant 4 at a second contact point. The distance between the first and second contact points in the pd direction is then used to calculate a vv parameter and a pd parameter such that the femoral implant 3 is in stable contact with the tibial implant 4 at two contact points. This results in a virtual joint pose J' which exhibits amended parameter values $vv_{J'}$ and $pd_{J'}$ and in which the other parameter values are identical to those of the target joint pose. A detailed description of this approach is given in the patent application PCT/EP2012/061757.

Since the target joint pose J and the virtual joint pose J' differ only in their vv and pd parameter values, the pose deviation value can be calculated from the difference in these parameter values alone. In particular, the pose deviation value can be calculated using the equation $$\text{poseDeviationValue} = [(pd_J - pd_{J'})^2 + (vv_J - vv_{J'})^2]^{1/2}.$$

FIG. 8 shows the femur 1 together with the femoral implant 3 and the tibia 2 together with the tibial implant 4 in a target joint pose (in the left-hand illustration) and in a virtual joint pose (in the right-hand illustration), in order to explain another approach for calculating the pose deviation value.

FIG. 8 shows a working plane 14 which is parallel to the plane spanned by the x-axis and the y-axis of the tibial co-ordinate system 9. In this example, the origin of the tibial co-ordinate system 9 lies in the working plane 14. However, the working plane 14 can have any other location as long as it is kept constant with respect to the tibia 2.

Two epicondylar points epiM and epiL are shown on the tibia 2. The distances between each of the epicondylar points epiM and epiL and the working plane 14 for the target pose and the virtual pose are used to calculate the pose deviation value. $d_{med}$ and $d_{lat}$ are the distances for the target pose, and $d_{med'}$ and $d_{lat'}$ are the distances for the virtual pose. The pose deviation value can then be calculated using the equation $$\text{poseDeviationValue} = [(d_{med} - d_{med'})^2 + (d_{lat} - d_{lat'})^2]^{1/2}.$$

FIG. 9 schematically shows a system 15 for carrying out the method as described above. The system comprises a computer 16 which is connected to an input unit 20, such as a keyboard, and to a display unit 21, such as a monitor. The computer 16 comprises a processing unit 17 which is connected to a memory unit 18 and an interface 19. The CPU can acquire data, such as the target poses, via the interface 19. The memory unit 18 stores a program code to be executed by the processing unit 17 and optionally also stores any data received via the interface 19. The processing unit 17 is adapted to execute the code stored in the memory unit 18, such that the processing unit 17 carries out the method steps as described above. The processing unit 17 is in particular then adapted to acquire the set of target poses, calculate a set of corresponding virtual poses for a pair of virtual test implant positions, calculate a pose deviation value for each target pose and calculate an overall pose deviation value from all the individual pose deviation values. The processing unit 17 is also adapted to repeat these steps for different pairs of virtual test implant positions in order to find a pair of virtual test implant positions for which the overall pose deviation value fulfils a predetermined minimisation criterion.

Information can be inputted into the computer 16 via the input unit 20, for example in order to limit the ranges of values for the pairs of virtual test implant positions. The display unit 21 is adapted to display the results determined by the processing unit 17, such as the calculated implant positions.

FIGS. 10a and 10b comprise graphs showing deviations between target poses and virtual poses determined using the classic planning (CPL), leg alignment (LA) and the present invention (6dof), respectively, over the range of motion, i.e. a range of flexion angles of the knee joint. The graph of FIG. 10a shows the deviations with regards to the pd shift (pdDev) and the graph of FIG. 10b shows the deviations with regards to the vv rotation (vvDev). More precisely, pdDev and vvDev are calculated as pdDev=$pd_j$-$pd_{j'}$ and vvDev=$vv_j$-$vv_{j'}$, respectively, as explained with reference to FIG. 7. Results of the classic planning approach are plotted in a dotted line, results of the leg alignment approach are plotted in a dashed line and results of the approach according to the present invention are plotted in a continuous line.

The target poses represent measured poses of the knee joint. The virtual poses represent the poses which would result if the implants would be implanted according to the implant positions determined according to the classic planning approach, the leg alignment approach and the approach according to the present invention, respectively. They can be compared to the target poses of the knee joint over the knee joint's range of motion. The range of motion applied in FIGS. 10a and 10b yields from a variation of the flexion angle from 0 degrees to 92 degrees. The flexion angles are for example derived from the target poses.

The graphs show that no approach results in implant positions which cause the target poses and the virtual poses to be identical over the whole range of motion. The reason is that the shapes of the implants are not identical to the shapes of the original bones, such that it is impossible to achieve the original kinematics of the joint over the whole range of motion, no matter how the implants are positioned. For some flexion angles, the present invention even yield worse virtual poses, i.e. larger deviations, than the leg alignment approach or the classic planning approach. But overall, i.e. over the whole range of motion, the average deviations are lower than those for implant positions determined using the classic planning approach or the leg alignment approach.

FIG. 11 shows a table comprising numerical values for the twelve parameters of the implant positions in the example scenario which lead to the deviations shown in FIG. 10. The values in the second column have been determined using the leg alignment approach. Initial values have been determined using classic planning, and the values for $pd_t$, $ap_f$ and $ie_f$ have then been optimised. The values in the third column have been determined using the approach according to the invention for six degrees of freedom. This means that the values for the six parameters $pd_t$, $ap_f$, $ie_f$, $pd_f$, $ie_t$ and $fe_t$ have been optimised as compared to the leg alignment approach, wherein the $ap_f$ parameter has been constrained to a small posterior range only. The fourth column shows the differences between the values obtained by the leg alignment approach and the approach according to the invention. No values are shown in this column for parameters which have not been optimised.

The invention claimed is:

1. A data processing system, comprising a computer having a processor configured to execute a computer-implemented method for determining implant positions of two implant components relative to two bones, wherein each of the implant components is to be attached to one of the bones such that the implant components form a joint between the bones, and wherein an implant position is a relative position between the implant component and the corresponding bone, said method comprising the steps of:
   a) acquiring, by the processor, a set of target poses, wherein a target pose represents a relative position to be achieved between the two bones, and the target poses are determined by recording poses of the two bones before joint replacement, mirroring a corresponding joint, or providing predefined poses that represent a desired kinematics of the joint;
   b) calculating, by the processor, a set of virtual poses for a pair of virtual test implant positions, wherein the set of virtual poses comprises one virtual pose for each of the target poses and wherein a virtual pose represents a relative position between the two bones if the virtual test implant positions were applied as the implant positions, wherein calculating the virtual pose takes into account the mechanical interaction of at least a portion of surrounding soft tissue structures;
   c) calculating, by the processor, a pose deviation value for each of the target poses, wherein a pose deviation value represents the difference between a target pose and the corresponding virtual pose;
   d) calculating, by the processor, an overall pose deviation value from all the individual pose deviation values;
   e) repeating steps b) to d) for different pairs of virtual test implant positions until the overall pose deviation value fulfils a minimisation criterion; and
   f) using, by the processor, the pair of virtual test implant positions for which the minimisation criterion is fulfilled as the implant positions for a surgical therapy plan.

2. A data processing method, performed by a computer, for determining implant positions of two implant components relative to two bones, wherein each of the implant components is to be attached to one of the bones such that the implant components form a joint between the bones, and wherein an implant position is a relative position between the implant component and the corresponding bone, said method comprising executing, by a processor of the computer, the steps of:
   a) acquiring a set of target poses, wherein a target pose represents a relative position to be achieved between the two bones, and the target poses are determined by recording poses of the two bones before joint replacement, mirroring a corresponding joint, or providing predefined poses that represent a desired kinematics of the joint;
   b) calculating a set of virtual poses for a pair of virtual test implant positions, wherein the set of virtual poses comprises one virtual pose for each of the target poses and wherein a virtual pose represents a relative position between the two bones if the virtual test implant positions were applied as the implant positions, wherein calculating the virtual pose takes into account the mechanical interaction of at least a portion of surrounding soft tissue structures;
   c) calculating a pose deviation value for each of the target poses, wherein a pose deviation value represents the difference between a target pose and the corresponding virtual pose;
   d) calculating an overall pose deviation value from all the individual pose deviation values;
   e) repeating steps b) to d) for different pairs of virtual test implant positions until the overall pose deviation value fulfils a minimisation criterion; and
   f) using the pair of virtual test implant positions for which the minimisation criterion is fulfilled as the implant positions for a surgical therapy plan.

3. The method according to claim 2, wherein calculating a virtual pose involves determining a relative position between the implant components in which they are in stable contact.

4. The method according to claim 3, wherein a virtual pose is defined by six parameters corresponding to six degrees of freedom, and calculating a virtual pose involves fixing four of the six parameters and varying the remaining two parameters until stable contact is achieved.

5. The method according to claim 2, wherein a pose is represented by the relative position of a co-ordinate system of one of the bones in a co-ordinate system of the other bone.

6. The method according to claim 5, wherein the orientations of the co-ordinate systems match the proximodistal, anterioposterior and mediolateral directions.

7. The method according to claim 2, wherein a pose is represented by the relative position of a co-ordinate system of one of the implant components in a co-ordinate system of the other implant component.

8. The method according to claim 7, wherein a first pose represented by the relative position of the co-ordinate systems which are not co-ordinate systems of the implant components is transformed into the pose represented by the relative position of the co-ordinate systems of the implant components.

9. The method according to claim 2, wherein the overall pose deviation value is calculated from weighted pose deviation values.

10. The method according to claim 2, wherein boundaries are defined for the virtual test implant positions.

11. The method according to claim 2, wherein a virtual test implant position is defined by six parameters corresponding to six degrees of freedom, thus resulting in twelve degrees of freedom for the two implant components, wherein the virtual test implant positions are varied in less than twelve degrees of freedom, and the parameters for the remaining degrees of freedom are set to fixed values.

12. The method according to claim 2, wherein the pose deviation values are calculated from the deviation between the virtual poses and the target poses with respect to a varus-valgus rotation and a proximodistal shift only.

13. The method according to claim 2, wherein a pose deviation value is calculated from the distances between each of two points on one of the bones and corresponding points on the other bone.

14. The method according to claim 2, wherein calculating the pose deviation values involves weighting the parameters corresponding to translational shifts and/or the parameters corresponding to rotational shifts.

15. A non-transitory computer-readable program storage medium storing a program which, when executed on a processor of a computer, causes the processor to perform the steps of:
   a) acquiring a set of target poses, wherein a target pose represents a relative position to be achieved between the two bones, and the target poses are determined by recording poses of the two bones before joint replacement, mirroring a corresponding joint, or providing predefined poses that represent a desired kinematics of the joint;
   b) calculating a set of virtual poses for a pair of virtual test implant positions, wherein the set of virtual poses comprises one virtual pose for each of the target poses and wherein a virtual pose represents a relative position between the two bones if the virtual test implant positions were applied as the implant positions, wherein calculating the virtual pose takes into account the mechanical interaction of at least a portion of surrounding soft tissue structures;
   c) calculating a pose deviation value for each of the target poses, wherein a pose deviation value represents the difference between a target pose and the corresponding virtual pose;
   d) calculating an overall pose deviation value from all the individual pose deviation values;
   e) repeating steps b) to d) for different pairs of virtual test implant positions until the overall pose deviation value fulfils a minimisation criterion; and
   f) using the pair of virtual test implant positions for which the minimisation criterion is fulfilled as the implant positions for a surgical therapy plan.

16. A computer comprising the non-transitory computer-readable program storage medium of claim 15.

17. A device for determining implant positions of two implant components relative to two bones, comprising a computer according to claim 16.

\* \* \* \* \*